(12) United States Patent
Davio et al.

(10) Patent No.: US 9,051,428 B2
(45) Date of Patent: Jun. 9, 2015

(54) BRANCHED ORGANOPOLYSILOXANES

(75) Inventors: Delphine Davio, Le Roeulx (BE);
Robert Alan Ekeland, Greer, SC (US);
Andreas Stammer, Pont-a-Celles (BE);
Giada Tonet, Chap.-lez-Herlaimont (BE)

(73) Assignee: Dow Corning Corporation, Midland, MI (US)

( * ) Notice: Subject to any disclaimer, the term of this patent is extended or adjusted under 35 U.S.C. 154(b) by 112 days.

(21) Appl. No.: 13/260,933

(22) PCT Filed: Mar. 30, 2010

(86) PCT No.: PCT/US2010/029111
§ 371 (c)(1),
(2), (4) Date: Sep. 29, 2011

(87) PCT Pub. No.: WO2010/117744
PCT Pub. Date: Oct. 14, 2010

(65) Prior Publication Data
US 2012/0022210 A1 Jan. 26, 2012

Related U.S. Application Data

(62) Division of application No. 61/164,990, filed on Mar. 31, 2009.

(51) Int. Cl.
*C08G 77/08* (2006.01)
*C07F 9/06* (2006.01)
*C08G 77/16* (2006.01)

(52) U.S. Cl.
CPC ............... *C08G 77/08* (2013.01); *C07F 9/065* (2013.01); *C08G 77/16* (2013.01)

(58) Field of Classification Search
USPC ........................................................ 528/23
See application file for complete search history.

(56) References Cited

U.S. PATENT DOCUMENTS

| 4,312,801 | A | 1/1982 | Hiriart Bodin et al. |
| 5,210,131 | A | 5/1993 | Gilson et al. |
| 5,424,385 | A | 6/1995 | Hager et al. |
| 5,457,220 | A | 10/1995 | Razzano |
| 5,674,938 | A | 10/1997 | Rautschek et al. |
| 5,773,548 | A | 6/1998 | Schickmann et al. |
| 6,001,928 | A | 12/1999 | Harkness et al. |
| 6,048,819 | A | 4/2000 | Habimana |
| 6,054,548 | A | 4/2000 | Currie et al. |
| 6,150,488 | A | 11/2000 | Martin |
| 6,448,196 | B1 | 9/2002 | Eglin et al. |
| 6,605,183 | B1 | 8/2003 | Rautschek et al. |
| 7,262,312 | B2 | 8/2007 | Sheridan et al. |
| 8,344,087 | B2 | 1/2013 | Maton et al. |
| 2002/0058112 | A1* | 5/2002 | Branlard et al. ............... 427/428 |
| 2003/0212197 | A1 | 11/2003 | Sakamoto et al. |

FOREIGN PATENT DOCUMENTS

WO  2006106362  10/2006

* cited by examiner

*Primary Examiner* — Kuo-Liang Peng
(74) *Attorney, Agent, or Firm* — Warner Norcross & Judd LLP

(57) ABSTRACT

The invention relates to branched organopolysiloxanes and to their preparation and use. A branched organopolysiloxane is prepared by the reaction of an alkoxysilane with a substantially linear organopolysiloxane containing at least one hydroxyl or hydrolysable group bonded to silicon, in the presence of a phosphazene catalyst. The branched organopolysiloxanes obtained can be suitable for use in a moisture curable sealant composition capable of curing to a high modulus seal, with less tendency to gel than when using other siloxane polycondensation catalysts. Phosphazene catalysts also have the advantage that the content of undesired low molecular weight cyclic silicones in the polymerization product is low.

9 Claims, No Drawings

BRANCHED ORGANOPOLYSILOXANES

CROSS REFERENCE TO RELATED APPLICATIONS

This application is a U.S. national stage filing under 35 U.S.C. §371 of PCT Application No. PCT/US10/29111 filed on 30 Mar. 2010, currently pending, which claims the benefit of U.S. Provisional Patent Application No. 61/164,990 filed 31 Mar. 2009 under 35 U.S.C. §119 (e). PCT Application No. PCT/US10/29111 and U.S. Provisional Patent Application No. 61/164,990 are hereby incorporated by reference.

This invention relates to branched organopolysiloxanes and to their preparation and use. The term branched is used in this invention to describe a polymer with more than two end groups.

Organopolysiloxanes have a wide variety of uses, for example as sealants, antifoams, elastomers, pressure sensitive adhesives, or release agents or in hair care or other personal care or household care compositions. In some of these uses, branched organopolysiloxanes have advantages over linear organopolysiloxanes. For example, branched organopolysiloxanes show improved properties as antifoams versus linear materials.

We have also found that branched organopolysiloxanes are useful in sealant compositions which cure to a high modulus seal. Compared to linear polysiloxanes, they allow formulation of higher modulus sealants while maintaining the rheology of the uncured sealant in an acceptable range.

We have also found that in personal care products, particularly cosmetic formulations applied to skin or hair, branched organosiloxanes are useful due to their increased wash off resistance compared to linear organosiloxanes.

Branched organopolysiloxanes can in general be prepared by a polycondensation reaction of a linear organopolysiloxane containing functional groups such as Si—OH groups with an alkoxysilane or other branching agent containing more than two reactive groups per molecule. However branching is not always easy to control and can lead to gelation. The branched structure can be controlled when introducing branching by the hydrosilylation reaction of Si—H groups with alkenyl groups, but this requires special polysiloxane starting materials containing Si—H groups and the use of costly platinum catalyst.

In a process according to the invention for the preparation of a branched organopolysiloxane by the reaction of an alkoxysilane with a substantially linear organopolysiloxane containing at least one hydroxyl or hydrolysable group bonded to silicon, characterized in that the reaction is carried out in the presence of a phosphazene catalyst.

The invention also includes a moisture curable sealant composition capable of curing to a high modulus seal, comprising a branched organopolysiloxane prepared as described above, a crosslinking agent reactive with the organopolysiloxane and a catalyst for siloxane condensation.

From another aspect, the invention comprises use of the branched organopolysiloxane reaction product of an alkoxysilane with a substantially linear organopolysiloxane containing at least one hydroxyl or hydrolysable group bonded to silicon in the presence of a phosphazene catalyst as a moisture curable sealant composition capable of curing to a high modulus seal.

We have found that the use of a phosphazene catalyst in the polycondensation reaction produces branched organopolysiloxanes, suitable for use in a moisture curable sealant composition capable of curing to a high modulus seal, with less tendency to gel than when using other siloxane polycondensation catalysts. Phosphazene catalysts also have the advantage that the content of undesired low molecular weight cyclic silicones in the polymerisation product is low.

The substantially linear organopolysiloxane generally contains on average more than one hydroxyl or hydrolysable group bonded to silicon, preferably terminal hydroxyl or hydrolysable groups. The polymer can for example have the general formula

$$X^1\text{—}A'\text{—}X^2 \tag{1}$$

where $X^1$ and $X^2$ are independently selected from silicon containing groups which contain hydroxyl or hydrolysable substituents and A' represents a polymer chain. Examples of $X^1$ or $X^2$ groups incorporating hydroxyl and/or hydrolysable substituents include groups terminating as described below:

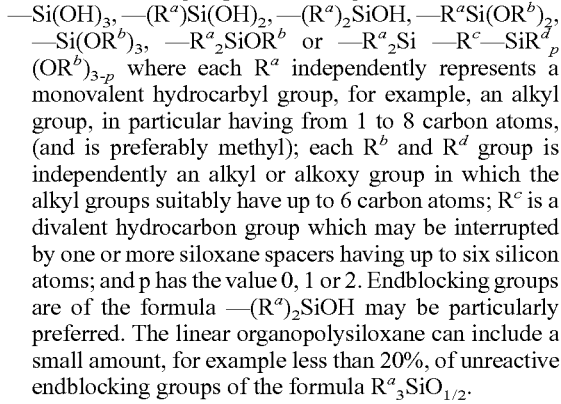

—Si(OH)$_3$, —(R$^a$)Si(OH)$_2$, —(R$^a$)$_2$SiOH, —R$^a$Si(OR$^b$)$_2$, —Si(OR$^b$)$_3$, —R$^a$$_2$SiOR$^b$ or —R$^a$$_2$Si—R$^c$—SiR$^d_p$(OR$^b$)$_{3-p}$ where each R$^a$ independently represents a monovalent hydrocarbyl group, for example, an alkyl group, in particular having from 1 to 8 carbon atoms, (and is preferably methyl); each R$^b$ and R$^d$ group is independently an alkyl or alkoxy group in which the alkyl groups suitably have up to 6 carbon atoms; R$^c$ is a divalent hydrocarbon group which may be interrupted by one or more siloxane spacers having up to six silicon atoms; and p has the value 0, 1 or 2. Endblocking groups are of the formula —(R$^a$)$_2$SiOH may be particularly preferred. The linear organopolysiloxane can include a small amount, for example less than 20%, of unreactive endblocking groups of the formula R$^a$$_3$SiO$_{1/2}$.

The polymer chain A' is preferably a polydiorganosiloxane chain comprising siloxane units of formula (2)

$$\text{—(R}^2{}_2\text{SiO)—} \tag{2}$$

in which each $R^2$ is independently an organic group such as a hydrocarbon group having from 1 to 18 carbon atoms, a substituted hydrocarbon group having from 1 to 18 carbon atoms or a hydrocarbonoxy group having up to 18 carbon atoms.

Examples of hydrocarbon groups $R^2$ include methyl, ethyl, propyl, butyl, vinyl, cyclohexyl, phenyl and tolyl groups. Substituted hydrocarbon groups have one or more hydrogen atoms in a hydrocarbon group replaced with another substituent, for example a halogen atom such as chlorine, fluorine, bromine or iodine, an oxygen atom containing group such as acrylic, methacrylic, alkoxy or carboxyl, a nitrogen atom containing group such as an amino, amido or cyano group, or a sulphur atom containing group such as a mercapto group. Examples of substituted hydrocarbon groups include a propyl group substituted with chlorine or fluorine such as 3,3,3-trifluoropropyl, chlorophenyl, beta-(perfluorobutyl)ethyl or chlorocyclohexyl group. Preferably, at least some and more preferably substantially all of the groups $R^2$ are methyl. Preferably the polydiorganosiloxanes are polydialkylsiloxanes, most preferably polydimethylsiloxanes.

Polydiorganosiloxanes comprising units of the formula (2) may be homopolymers or copolymers. Mixtures of different polydiorganosiloxanes are also suitable. In the case of polydiorganosiloxane co-polymers the polymeric chain may comprise a combination of blocks made from chains of units depicted in figure (2) above where the two $R^2$ groups are:
  both alkyl groups (preferably both methyl or ethyl), or
  alkyl and phenyl groups, or
  alkyl and fluoropropyl, or
  alkyl and vinyl or
  alkyl and hydrogen groups.

Typically at least one block will comprise siloxane units in which both $R^2$ groups are alkyl groups.

The polymer (A) may alternatively have a block copolymeric backbone comprising at least one block of siloxane groups of the type depicted in formula (2) above and at least one block comprising any suitable organic polymer chain. Examples of suitable organic polymer chains are polyacrylic, polyisobutylene and polyether chains.

The substantially linear organopolysiloxane containing at least one hydroxyl or hydrolysable group bonded to silicon generally has a degree of polymerization such that its viscosity at 25° C. is between 5 mPa·s and 5000 mPa·s, preferably between 10 mPa·s and 500 mPa·s.

The alkoxysilane which is reacted with the linear organopolysiloxane preferably contains an average of more than 2 silicon-bonded alkoxy groups per molecule. The alkoxy groups preferably each have 1 to 4 carbon atoms and most preferably are methyl or ethyl groups. The alkoxysilane can for example comprise a trialkoxysilane of the formula R'Si(OR)$_3$, where R represents an alkyl group having 1 to 4 carbon atoms and R' represents a monovalent hydrocarbon or substituted hydrocarbon group having 1 to 18 carbon atoms. Examples of such groups R' include alkyl groups, for example methyl, ethyl, propyl, butyl, hexyl, octyl, 2-ethylhexyl, lauryl or stearyl; cycloalkyl groups, for example cyclopentyl or cyclohexyl); alkenyl groups, for example vinyl, allyl or hexenyl; aryl groups, for example phenyl or tolyl; aralkyl groups, for example 2-phenylethyl; and groups obtained by replacing all or part of the hydrogen in the preceding organic groups with halogen, for example 3,3,3-trifluoropropyl. Examples of preferred trialkoxysilanes include methyltrimethoxysilane, methyltriethoxysilane, isobutyltrimethoxysilane, n-octyltriethoxysilane, n-octyltrimethoxysilane, ethyltrimethoxysilane, ethyltriethoxysilane, vinyltrimethoxysilane, vinyltriethoxysilane, phenyltrimethoxysilane and 3,3,3-trifluoropropyltrimethoxysilane. Trialkoxysilanes having a long chain alkyl group R' having for example 6 to 18 carbon atoms, for example n-octyltrimethoxysilane, react with the linear organopolysiloxane to form a branched organopolysiloxane having a long chain alkyl group, for example an octyl group, at the branching point. The presence of such a long chain alkyl group increases the compatibility of the branched organopolysiloxane with organic materials, for example hydrocarbon solvents or organic polymers.

The alkoxysilane can alternatively be a tetraalkoxysilane such as tetraethoxysilane (tetraethyl orthosilicate). Reaction of the linear organopolysiloxane with a tetraalkoxysilane can form a branched organopolysiloxane having Si-alkoxy functionality in the polysiloxane chain as well as branching.

The alkoxysilane can be a partially condensed alkoxysilane in which some alkoxy groups have been hydrolysed and condensed to form siloxane linkages and some alkoxy groups remain bonded to silicon. Such a partially condensed alkoxysilane preferably contains on average more than two alkoxy groups per molecule bonded to silicon. The alkoxysilane can for example be an oligomeric partially condensed trialkoxysilane. Such an oligomer may have a branched structure as well as Si-alkoxy groups to provide further branching sites. Tetraalkoxysilanes can also be used in partially condensed form; for example partially condensed tetraethoxysilane containing SiO$_2$ branching units is widely available.

The alkoxysilane and the substantially linear organopolysiloxane containing at least one hydroxyl or hydrolysable group bonded to silicon are preferably reacted in amounts such that the molar ratio of Si-bonded alkoxy groups in the alkoxysilane to hydroxyl or hydrolysable groups in the substantially linear organopolysiloxane is from 1:100 to 1:1, more preferably 1:40 to 1:2. If the substantially linear organopolysiloxane has hydrolysable groups rather than hydroxyl groups, it may be suitable for a controlled amount of moisture to be present during the reaction. The branched organopolysiloxane may contain reactive terminal Si—OH or Si-alkoxy groups.

The phosphazene catalyst for the reaction of the alkoxysilane with the hydroxyl-containing substantially linear organopolysiloxane generally contains at least one —(N=P<)— unit and is usually an oligomer having up to 10 such phosphazene units, for example having an average of from 1.5 up to 5 phosphazene units. The phosphazene catalyst can for example be a halophosphazene, particularly a chlorophosphazene (phosphonitrile chloride), an oxygen-containing halophosphazene, a phosphazene base or an ionic derivative of a phosphazene such as a phosphazenium salt, particularly an ionic derivative of a phosphonitrile halide such as a perchlorooligophosphazenium salt.

One particularly suitable type of phosphazene catalyst is an oxygen-containing halophosphazene, particularly an oxygen-containing chlorophosphazene. Such an oxygen-containing chlorophosphazene can for example have the formula Cl(PCl$_2$=N)$_n$—P(O)Cl or HO(PCl$_2$=N)$_n$—P(O)Cl$_2$. The average value of n can for example be in the range 1 to 10, particularly 1 to 5. The catalyst may also comprise tautomers of the catalyst of the formula HO(PCl$_2$=N)$_n$—P(O)Cl$_2$. Another type of suitable oxygen-containing chlorophosphazene has the formula Z'O(PCl$_2$=N)$_n$—P(O)Cl$_2$ in which Z' represents an organosilicon radical bonded to phosphorus via oxygen, for example a phosphazene catalyst of the formula R"$_3$SiO(PCl$_2$=N)$_n$—P(O)Cl$_2$ where each R" represents a monovalent hydrocarbon or substituted hydrocarbon group having 1 to 18 carbon atoms. The catalyst may also comprise condensation products of such an organosilicon-containing phosphazene. All or some of the chlorine atoms in any of the above oxygen-containing phosphazenes can be replaced by radicals Q, in which Q represents the hydroxyl group, monovalent organic radicals, such as alkoxy radicals or aryloxy radicals, halogen atoms other than chlorine, organosilicon radicals and phosphorus-containing radicals, although this is not preferred.

Another suitable type of phosphazene catalyst is a perchlorooligophosphazenium salt of the formula

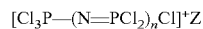

where n has an average value in the range 1 to 10 and Z represents an anion. The anion is preferably a complex anion and can for example be of the formula MX$_{v+1}$ in which M is an element having an electronegativity on Pauling's scale of from 1.0 to 2.0 and valency v and X is a halogen atom. The element M can for example be phosphorus or antimony. The anion Z can alternatively be a complex anion of the formula [MX$_{v-y+1}$R$^3_y$]— wherein R$^3$ is an alkyl group having 1 to 12 carbon atoms and y has a value between 0 and v, as described in U.S. Pat. No. 5,457,220.

The phosphazene catalyst can alternatively be a phosphazene base, particularly an aminated phosphazene as described in U.S. Pat. No. 6,001,928, U.S. Pat. No. 6,054,548 or U.S. Pat. No. 6,448,196. Such a phosphazene base can be formed by reaction of a perchlorooligophosphazenium salt with a secondary amine followed by ion exchange reaction with a basic nucleophile. The secondary amine is for example of the formula HNR$^4_2$, and some or all of the chlorophosphazene oligomer are replaced by —NR$^4_2$ groups.

The phosphazene catalyst is typically present at 1 or 2 up to 200 parts per million based on the combined weight of alkoxysilane and substantially linear organopolysiloxane, for example at 5 to 50 parts per million. The reaction between the alkoxysilane and substantially linear organopolysiloxane can be carried out at ambient temperature but is preferably carried out at elevated temperature, for example in the range 50 to 100° C.

The extent of polymerization during the process of the invention is preferably such that the branched organopolysiloxane produced has a weight average molecular weight Mw at least five times, more preferably at least ten times, the Mw of the starting organopolysiloxane. The Mw can be measured by gel permeation chromatography (GPC). The Mw of the branched organopolysiloxane produced is preferably at least 10,000, more preferably at least 100,000, and may be as high as 1,000,000 or more. The reaction can be terminated by adding a neutraliser when a desired degree of polymerization has been reached. The neutralizer can for example be a trialkylamine in the case of the catalysts described in U.S. Pat. No. 5,457,220.

The branched organopolysiloxanes obtained using the phosphazene catalyst in the above process have a high weight average molecular weight Mw and show a broad molecular weight distribution. The branched organopolysiloxanes have acceptable rheology, that is they are not too stiff to be shaped when uncured, despite their high Mw.

The reaction between the alkoxysilane and substantially linear organopolysiloxane can be carried out in the presence of an inert diluent or in the absence of any diluent. The presence of a liquid diluent generally allows the formation of higher molecular weight branched polymers while keeping a fluid product. A liquid diluent can for example be a solvent for the substantially linear organopolysiloxane and/or the alkoxysilane or can be a non-solvent. The diluent can be a silicone based and/or organic based diluent and is generally chosen to have no groups reactive with the alkoxysilane or with the substantially linear organopolysiloxane. The diluent may be chosen from materials whose presence is desired as an extender and/or plasticizer in the end product formulation based on the branched organopolysiloxane produced.

Any suitable solvent or diluent or combination of diluents may be used in the reaction mixture. In general any of the extenders used in WO-A-2006/106362 can be used. These include each of the following alone or in combination with others from the list:
hydrocarbon oils such as mineral oil fractions comprising linear (e.g. n-paraffinic) mineral oils, branched (iso-paraffinic) mineral oils, and/or cyclic (referred in some prior art as naphthenic) mineral oils, the hydrocarbons in the oil fractions comprising from 5 to 25 carbon atoms per molecule;
trialkylsilyl terminated polydialkyl siloxane where the alkyl groups are preferably methyl groups, where each alkyl group may be the same or different and comprises from 1 to 6 carbon atoms but is preferably a methyl group, preferably with a viscosity of from 100 to 100000 mPa·s at 25° C. and most preferably from 1000 to 60000 mPa·s at 25° C.;
polyisobutylenes (PIB);
phosphate esters such as trioctyl phosphate;
polyalkylbenzenes, linear and/or branched alkylbenzenes such as heavy alkylates, dodecyl benzene and other alkylarenes;
esters of aliphatic monocarboxylic acids;
linear or branched mono unsaturated hydrocarbons such as linear or branched alkenes or mixtures thereof containing from 8 to 25 carbon atoms;
natural oils and derivatives thereof.

Preferred diluents include the mineral oil fractions, alkylcycloaliphatic compounds and alkybenzenes including polyalkylbenzenes. Any suitable mixture of mineral oil fractions may be used as diluent but high molecular weight extenders, for example having a molecular weight above 220, are particularly preferred. Examples include alkylcyclohexanes of molecular weight above 220), paraffinic hydrocarbons and mixtures thereof containing from 1 to 99%, preferably from 15 to 80% n-paraffinic and/or isoparaffinic hydrocarbons (linear branched paraffinic) and 1 to 99%, preferably 85 to 20% cyclic hydrocarbons (naphthenic) and a maximum of 3%, preferably a maximum of 1% aromatic carbon atoms. The cyclic paraffinic hydrocarbons (naphthenics) may contain cyclic and/or polycyclic hydrocarbons.

Alternative preferred diluents suitable for retaining in many products as an extender or plasticiser comprise non-mineral based natural oils, i.e. oils derived from animals, seeds or nuts and not from petroleum. Such natural oils are generally triglycerides of mixtures of fatty acids, particularly mixtures containing some unsaturated fatty acid. Diluents containing natural oils may for example be preferred for use in some personal care products. The diluent can be a derivative of a natural oil such as a transesterified vegetable oil, a boiled natural oil, a blown natural oil, or a stand oil (thermally polymerized oil).

The alkylbenzene compounds suitable for use as diluent include heavy alkylate alkylbenzenes and alkylcycloaliphatic compounds. Examples of alkyl substituted aryl compounds useful as diluents are compounds which have aryl groups, especially benzene substituted by alkyl and possibly other substituents, and a molecular weight of at least 200. Examples of such diluents useful as extenders are described in U.S. Pat. No. 4,312,801.

The amount of diluent, if used, can for example be up to 70%, usually 5 to 70%, of the combined weight of alkoxysilane, substantially linear organopolysiloxane and diluent. A diluent whose presence is required as an extender or plasticizer in the branched organopolysiloxane formulation will often be used at 25 to 60% of the combined weight of alkoxysilane, substantially linear organopolysiloxane and diluent. Non-reactive additives whose presence is required in the branched organopolysiloxane formulation, for example heat stabilizers, flame retardants, UV stabilizers, fungicides, biocides or perfumes, may be dissolved in the diluent.

The diluent can alternatively be a solid such as a wax, preferably having a melting point in the range 30 to 100° C. The wax can for example be a hydrocarbon wax such as a petroleum-derived wax, or a wax comprising carboxylic esters such as beeswax, lanolin, tallow, carnauba, candelilla, tribehenin or a wax derived from plant seeds, fruits, nuts or kernel, including softer waxes referred to as 'butter', for example mango butter, shea butter or cocoa butter. The wax can alternatively be a polyether wax or a silicone wax.

The branched organopolysiloxanes produced according to the present invention are particularly suitable for use in sealants and antifoams but are also useful in personal care products and pressure sensitive adhesives. The branched organopolysiloxane product, optionally containing diluent, can be dissolved in an organic solvent or emulsified in water if the branched organopolysiloxane formulation is required in solution or emulsion form. For sealant use the branched organopolysiloxane product, optionally containing diluent, is generally used in the sealant formulation without further dilution.

A sealant composition comprising a branched organopolysiloxane prepared as described above is preferably a moisture curable sealant composition comprising the branched organopolysiloxane, a crosslinking agent reactive with the branched organopolysiloxane and a catalyst for siloxane condensation.

The crosslinking agent in such a sealant composition generally has groups reactive with the Si—OH and/or Si-alkoxy terminal groups of the branched organopolysiloxane. The crosslinking agent preferably contains at least two and preferably at least three groups reactive with the silicon-bonded hydroxyl or alkoxy groups of the branched organopolysiloxane. The reactive groups of the crosslinking agent are preferably silicon bonded hydrolysable groups. The crosslinking agent can for example be a silane or short chain organopolysiloxane, for example a polydiorganosiloxane having from 2 to about 100 siloxane units. The molecular structure of such an organopolysiloxane can be straight chained, branched, or cyclic. The crosslinking agent can alternatively be an organic polymer substituted by silicon-bonded hydrolysable groups.

The hydrolysable groups in the crosslinker can for example be selected from acyloxy groups (for example, acetoxy, octanoyloxy, and benzoyloxy groups); ketoximino groups (for example dimethyl ketoximo, and isobutylketoximino); alkoxy groups (for example methoxy, ethoxy, an propoxy) and/or alkenyloxy groups (for example isopropenyloxy and 1-ethyl-2-methylvinyloxy).

When the crosslinking agent is a silane having three silicon-bonded hydrolysable groups per molecule, the fourth group is suitably a non-hydrolysable silicon-bonded organic group. These silicon-bonded organic groups are suitably hydrocarbyl groups which are optionally substituted by halogen such as fluorine and chlorine. Examples of such fourth groups include alkyl groups (for example methyl, ethyl, propyl, and butyl); cycloalkyl groups (for example cyclopentyl and cyclohexyl); alkenyl groups (for example vinyl and allyl); aryl groups (for example phenyl, and tolyl); aralkyl groups (for example 2-phenylethyl) and groups obtained by replacing all or part of the hydrogen in the preceding organic groups with halogen. Preferably the fourth silicon-bonded organic group is methyl or ethyl.

Examples of crosslinking agents include acyloxysilanes, particularly acetoxysilanes such as methyltriacetoxysilane, vinyltriacetoxysilane, ethyl triacetoxysilane, di-butoxy diacetoxysilane and/or dimethyltetraacetoxydisiloxane, and also phenyl-tripropionoxysilane. The crosslinking agent can be an oxime-functional silane such as methyltris(methylethylketoximo)silane, vinyl-tris(methylethylketoximo)silane, or an alkoxytrioximosilane. The crosslinking agent can be an alkoxysilane, for example an alkyltrialkoxysilane such as methyltrimethoxysilane, methyltriethoxysilane, isobutyltrimethoxysilane or ethyltrimethoxysilane, an alkenyltrialkoxysilane such as vinyltrimethoxysilane or vinyltriethoxysilane, or phenyltrimethoxysilane, 3,3,3-trifluoropropyltrimethoxysilane, or ethylpolysilicate, n-propylorthosilicate, ethylorthosilicate, or an alkenyloxysilane such as methyltris(isopropenoxy)silane or vinyltris(isopropenoxy)silane. The crosslinking agent can alternatively be a short chain polydiorganosiloxane, for example polydimethylsiloxane, tipped with trimethoxysilyl groups or can be an organic polymer, for example a polyether such as polypropylene oxide, tipped with methoxysilane functionality such as trimethoxysilyl groups. The crosslinking agent used may also comprise any combination of two or more of the above.

Further alternative crosslinking agents include alkylalkenylbis(N-alkylacetamido) silanes such as methylvinyldi-(N-methylacetamido)silane, and methylvinyldi-(N-ethylacetamido)silane; dialkylbis(N-arylacetamido) silanes such as dimethyldi-(N-methylacetamido)silane; and dimethyldi-(N-ethylacetamido)silane; alkylalkenylbis(N-arylacetamido) silanes such as methylvinyldi(N-phenylacetamido)silane and dialkylbis(N-arylacetamido) silanes such as dimethyldi-(N-phenylacetamido)silane, or any combination of two or more of the above.

The amount of crosslinking agent present in the sealant composition will depend upon the particular nature of the crosslinking agent, particularly its molecular weight. The compositions suitably contain crosslinking agent in at least a stoichiometric amount as compared to the branched organopolysiloxane. Sealant compositions may contain, for example, from 2-30% by weight crosslinking agent, generally from 2 to 10%. For example, acetoxysilane or oximinosilane crosslinkers may typically be present in amounts of from 3 to 8% by weight.

The sealant composition further comprises a siloxane condensation catalyst. This increases the speed at which the composition cures. The catalyst chosen for inclusion in a particular silicone sealant composition depends upon the speed of cure required. Any suitable condensation catalyst may be used including compounds of tin, lead, antimony, iron, cadmium, barium, manganese, zinc, chromium, cobalt, nickel, titanium, aluminium, gallium or germanium and zirconium, for example organotin catalysts, organic salts of tin and 2-ethylhexoates of iron, cobalt, manganese, lead and zinc. Organotin, titanate and/or zirconate based catalysts are preferred.

Silicone sealant compositions which contain oximosilanes or acetoxysilanes generally use an organotin catalyst, for example a diorganotin dicarboxylate such as dibutyltin dilaurate, dimethyltin dibutyrate, dibutyltin diacetate, dimethyltin bisneodecanoate, dibutyltin dibenzoate, dimethyltin dineodeconoate or dibutyltin dioctoate.

For sealant compositions which include alkoxysilane crosslinking agents, the preferred curing catalysts are titanate or zirconate compounds including chelated titanates and zirconates. Titanate and/or zirconate based catalysts may comprise a compound according to the general formula $Ti[OR^4]_4$ where each $R^4$ may be the same or different and represents a monovalent, primary, secondary or tertiary aliphatic hydrocarbon group which may be linear or branched containing from 1 to 10 carbon atoms. Optionally the titanate may contain partially unsaturated groups. However, preferred examples of $R^4$ include but are not restricted to methyl, ethyl, propyl, isopropyl, butyl, tertiary butyl and a branched secondary alkyl group such as 2,4-dimethyl-3-pentyl. Alternatively, the titanate may be chelated. The chelation may be with any suitable chelating agent such as an alkyl acetylacetonate such as methyl or ethyl acetylacetonate.

Sealant compositions of this invention may contain, as optional constituents, other ingredients which are conventional to the formulation of silicone sealants. For example, the sealant compositions will normally contain one or more finely divided reinforcing fillers such as high surface area fumed and precipitated silicas including rice hull ash and/or calcium carbonate, which is to some extent a reinforcing filler. The sealant composition can additionally contain a nonreinforcing filler such as crushed quartz, diatomaceous earth, barium sulphate, iron oxide, titanium dioxide, carbon black, talc, wollastonite, aluminite, calcium sulphate (anhydrite), gypsum, calcium sulphate, magnesium carbonate, a clay such as kaolin, aluminium trihydroxide, magnesium hydroxide, graphite, copper carbonate, nickel carbonate, barium carbonate and/or strontium carbonate and/or electrically and/or heat conductive fillers.

Other ingredients which may be included in sealant compositions of the invention include but are not restricted to co-catalysts for accelerating the cure of the composition such as metal salts of carboxylic acids and amines, rheology modifiers, adhesion promoters, pigments, heat stabilizers, flame retardants, UV stabilizers, fungicides, biocides, and/or water scavengers, (typically the same compounds as those used as crosslinking agents, or silazanes).

The sealant compositions can be prepared by mixing the ingredients employing any suitable mixing equipment. For example, preferred one-part moisture curable compositions may be made by mixing the branched organopolysiloxane, optionally comprising a non-reactive silicone or organic fluid extender or plasticizer, with all or part of the filler, and mixing this with a pre-mix of the cros slinking agent and the catalyst under substantially anhydrous conditions. The resulting curable compositions are generally stored under substantially anhydrous conditions, for example in sealed containers, until required for use. Such one-part moisture curable compositions are stable in storage but cure on exposure to atmospheric moisture and may be employed in a variety of applications, particularly suitable for sealing joints, cavities and other spaces in articles and structures which are subject to relative movement, or for example as coating, caulking, mold making and encapsulating materials.

The sealant composition can alternatively be a two-part composition in which the branched organopolysiloxane and the crosslinking agent are packaged separately. In such a composition the catalyst can in general be packaged with either the polysiloxane or with the crosslinking agent. Both packages in such a two-part composition can be anhydrous for curing on exposure to atmospheric moisture, or one only of the packages may contain a controlled amount of moisture to speed up initial cure of the composition on mixing of the packages.

For use in personal care products, the branched organopolysiloxane product can for example be dissolved in an organic solvent or emulsified in water using an anionic, cationic, amphoteric and/or nonionic surfactant. If a personal care product, for example a cosmetic such as a skin cream, is required in organic solution form it may be convenient to react the alkoxysilane and substantially linear organopolysiloxane in solution in the organic solvent to be used in the personal care product.

Personal care formulations containing the branched polyorganosiloxane can contain various additives known in such formulations, for example perfumes, sunscreens, antioxidants, vitamins, drugs, biocides, pest repellents, catalysts, natural extracts, peptides, warming effect and cooling agents, fillers, colouring agents such as dyes, pigments and shimmers, heat stabilizers, flame retardants, UV stabilizers, fungicides, biocides, thickeners, preservatives, antifoams, freeze thaw stabilizers, or inorganic salts to buffer pH.

When a personal care product containing a branched organopolysiloxane according to the invention is applied to the skin or hair, the product is generally more resistant to washing off than a similar product containing a linear organopolysiloxane of similar molecular weight.

The invention is illustrated by the following Examples, in which parts and percentages are by weight. The molecular weight of the siloxanes in the mixtures was determined by gel permeation chromatography (GPC). The analyses have been performed by GPC (Alliance Waters 2690) using triple detection (Refractive index detector, Viscometer and Light Scattering Detectors) and toluene as solvent. Molecular weight averages were determined by universal calibration relative to a triple detection calibration realized on a single point using polystyrene narrow standard (Mw 70,950 g/mol).

Example 1

500 parts dimethylhydroxyl-terminated polydimethylsiloxane having a viscosity of 70 mPa·s at 25° C., a Mn of 2500 g/mol and a Mw of 3500 g/mol was mixed with 500 parts Hydroseal G 250H hydrocarbon oil extender (sold by Total), and 4.01 parts methyltrimethoxysilane (MTM). 20 parts per million (ppm) of an ionic phosphazene $[Cl(PCl_2=N)_xPCl_3]^+$ $[PCl_6]^-$ diluted in dichloromethane was added as catalyst. The polymerisation was carried out in a 1 l glass reactor (IKA) at 80° C. under vacuum. The polymerisation was stopped after 20 minutes by the addition of 0.05 parts trihexylamine. A branched polydimethylsiloxane polymer, mixed with the hydrocarbon oil extender, was produced.

Examples 2 to 5

Example 1 was repeated using different amounts of MTM (example 2 and 3) and alternative alkoxysilanes in place of the MTM (example 4 and 5):

Example 2—0.4 parts MTM, 29 minutes polymerization time

Example 3—0.8 parts MTM, 22 minutes polymerization time

Example 4—6.13 parts tetraethyl orthosilicate (TEOS, tetraethoxysilane), temperature 90° C., catalyst 40 ppm, 0.09 p trihexylamine, 131 minutes polymerization time Example 5—8.13 parts n-octyltriethoxysilane, temperature 90° C., catalyst 20 ppm, 0.45 p trihexylamine 32 minutes polymerization time Branched polydimethylsiloxane polymers, mixed with the hydrocarbon oil extender, were produced in each case.

The number average molecular weight Mn and the weight average molecular weight Mw of each branched polydimethylsiloxane were measured by GPC. The results, and the polydispersity index PI (ratio Mw/Mn) are shown in Table 1 below. The viscosity of the reaction product was measured by a Brookfield viscometer (Brookfield RVDV-I+, spindle 7 example 1-3, spindle 6 example 4 and 5 at 25° C.) and is also shown in Table 1.

TABLE 1

| Example | 1 | 2 | 3 | 4 | 5 |
|---|---|---|---|---|---|
| Mn (kg/mol) | 53 | 159 | 142 | 65 | 56 |
| Mw (kg/mol) | 906 | 407 | 525 | 959 | 994 |
| PI | 17.3 | 2.6 | 3.7 | 14.7 | 17.8 |
| Viscosity (mPas) | 15200 | 63800 | 64400 | 22600 | 14000 |

The branched polydimethylsiloxanes of Examples 1, 4 and 5 were characterized by Si29-NMR. The Si29-NMR showed that no self-condensation of the alkoxysilanes had occurred. The NMR result for Example 4 showed that some Si-alkoxy function had been retained in the branched polydimethylsiloxane. The NMR result for Example 5 showed incorporation of n-octyl groups on the polysiloxane chain at branching points.

Example 6

800 parts of the dimethylhydroxyl-terminated polydimethylsiloxane of Example 1 was mixed with 200 parts of a silicone wax having a melting point of about 32° C. (DC 2503 sold by Dow Corning) and 0.64 parts methyltrimethoxysilane (MTM) at 70° C. 20 parts per million (ppm) $[Cl(PCl_2=N)_xPCl_3]^+[PCl_6]^-$ diluted in dichloromethane was added as catalyst. The polymerisation was carried out in a 1 l glass reactor (IKA) at 70° C. under vacuum. The polymerisation was stopped after 54 minutes by the addition of 0.08 parts trihexylamine. A branched polydimethylsiloxane polymer blend with silicone wax was produced. The branched polydimethylsiloxane has Mn 112 kg/mol and Mw 176 kg/mol. The mixture has a viscosity of 324000 mPas (Brookfield as in example 1).

Example 7

500 parts of the dimethylhydroxyl-terminated polydimethylsiloxane of Example 1 was mixed with 500 parts of an isoparaffin (Isopar L supplied by Exxon) and 6.13 parts tetraethoxyorthosilicate (TEOS). 20 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 90° C. under vacuum. The polymerisation was stopped after 67 minutes by the addition of 0.05 parts trihexylamine. A branched polydimethylsiloxane dissolved in isoparaffin was produced. The branched polydimethylsiloxane has Mn 78 kg/mol and Mw 1546 kg/mol. The mixture has a viscosity of 17000 mPas. (Brookfield as in example 1)

The wash off resistance on skin of the branched silicone of Example 7 was evaluated by a number of washes with a surfactant solution (0.5% sodium lauryl ether sulfate in water) using FTIR spectroscopy. A linear polydimethylsiloxane with a Mw of 938 kg/mol was tested for comparison. Samples tested were diluted to 5% active in isododecane. The % of silicone found on the skin after various washes are indicated in Table 2.

TABLE 2

|  | Linear Polymer | Branched Polymer |
| --- | --- | --- |
| Before wash | 100 | 100 |
| wash 1 | 35.35 | 55.31 |
| wash 2 | 26.76 | 48.63 |
| wash 3 | 24.41 | 35.21 |

Example 8

500 parts of the dimethylhydroxyl-terminated polydimethylsiloxane of Example 1 was mixed with 500 parts Isopar L isoparaffin and 4.00 parts methyltrimethoxysilane (MTM). 20 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 80° C. under vacuum. The polymerisation was stopped after 20 minutes by the addition of 0.05 parts trihexylamine. A branched polydimethylsiloxane dissolved in isoparaffin was produced. The branched polydimethylsiloxane has Mn 89 kg/mol and Mw 1334 kg/mol. The mixture has a viscosity of 300000 mPas. (Brookfield as in example 1).

Example 9

400 parts of the dimethylhydroxyl-terminated polydimethylsiloxane of Example 1 was mixed with 400 parts of Xylene and 0.64 parts methyltrimethoxysilane (MTM). 20 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 80° C. under vacuum. The polymerisation was stopped after 52 minutes by the addition of 0.04 parts trihexylamine. A branched polydimethylsiloxane dissolved in xylene was produced. The branched polydimethylsiloxane has Mn 169 kg/mol and Mw 1002 kg/mol.

Example 10

395 parts of the dimethylhydroxyl-terminated polydimethylsiloxane of Example 1 and 100 parts methylphenylhydroxyl-terminated polymethylphenylsiloxane having a viscosity of approx. 500 mPa·s at 25° C. were mixed with 500 parts of Xylene, and 5 parts phenyltrimethoxysilane. 30 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 80° C. under vacuum. The polymerisation was stopped after 63 minutes by the addition of 0.075 parts trihexylamine. A branched polydimethyl methyphenylsiloxane copolymer dissolved in xylene was produced. The branched polydimethyl methyphenylsiloxane copolymer has Mn 82 kg/mol and Mw 1007 kg/mol. The mixture has a viscosity of 30000 mPas. (Brookfield as in example 1)

Example 11

1000 parts of the dimethylhydroxyl-terminated polydimethylsiloxane of Example 1 were mixed with 8.013 parts of methyltrimethoxysilane (MTM). 3 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 70° C. under vacuum. The polymerisation was stopped after 2 minutes by the addition of 0.025 parts trihexylamine. A branched polydimethylsiloxane was produced. The branched polydimethylsiloxane has Mn 63 kg/mol and Mw 178 kg/mol.

Examples 12 to 14

Example 11 was repeated using different amounts of MTM (example 12) and alternative alkoxysilanes in place of the MTM (example 13 and 14):

Example 12—4.006 parts MTM, 2 minutes polymerization time

Example 13—12.255 parts tetraethyl orthosilicate (TEOS, tetraethoxysilane), 2 minutes polymerization time Example 14—6.13 parts tetraethyl orthosilicate (TEOS, tetraethoxysilane), 2 minutes polymerization time Branched polydimethylsiloxane polymers, were produced in each case The number average molecular weight Mn and the weight average molecular weight Mw of each branched polydimethylsiloxane were measured by GPC. The results, and the polydispersity index PI (ratio Mw/Mn) are shown in Table 3 below.

TABLE 3

| Example | 12 | 13 | 14 |
| --- | --- | --- | --- |
| Mn (kg/mol) | 88 | 36 | 76 |
| Mw (kg/mol) | 218 | 98 | 159 |
| PI | 2.48 | 2.71 | 2.08 |

Example 15

800 parts of the dimethylhydroxyl-terminated polydimethylsiloxane of Example 1 was mixed with 200 parts Sunflower Oil (Sunflower Oil provided by Mosselman) and 6.41 parts methyltrimethoxysilane (MTM). 25 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 70° C. under vacuum. The polymerisation was stopped after 7 minutes by the addition of 0.134 parts trihexylamine. A branched polydimethylsiloxane dispersed in Sunflower Oil was produced. The branched polydimethylsiloxane has Mn 77 kg/mol and Mw 435 kg/mol.

Examples 16

800 parts of the dimethylhydroxyl-terminated polydimethylsiloxane of Example 1 was mixed with 200 parts Sunflower Oil (Sunflower Oil provided by Mosselman) and 0.321 parts methyltrimethoxysilane (MTM). 22.5 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 70° C. under vacuum. The polymerisation was stopped after 12 minutes by the addition of 0.151 parts trihexylamine. A branched polydimethylsiloxane dispersed in Sunflower Oil was produced. The branched polydimethylsiloxane has Mn 65 kg/mol and Mw 123 kg/mol.

Example 17

500 parts of the dimethylhydroxyl-terminated polydimethylsiloxane of Example 1 was mixed with 500 parts Isododecane (Isododecane provided by Ineos Oligomers) and 2.003 parts methyltrimethoxysilane (MTM). 10 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 60° C. under vacuum. The polymerisation was stopped after 7 minutes by the addition of 0.0419 parts trihexylamine. A branched polydimethylsiloxane dissolved in Isododecane was produced. The branched polydimethylsiloxane has Mn 128 kg/mol and Mw 1 153 kg/mol.

Example 18

500 parts of the dimethylhydroxyl-terminated polydimethylsiloxane of Example 1 was mixed with 500 parts Isopar L isoparaffin (see example 8) and 3.036 parts tetraethyl orthosilicate (TEOS, tetraethoxysilane). 7.5 parts per million (ppm) [Cl(PCl$_2$=N)$_x$PCl$_3$]$^+$[PCl$_6$]$^-$ diluted in dichloromethane was added as catalyst. The polymerisation was carried out in a 1 l glass reactor (IKA) at 80° C. under vacuum. The polymerisation was stopped after 33 minutes by the addition of 0.028 parts trihexylamine. A branched polydimethylsiloxane dissolved in isoparaffin was produced. The branched polydimethylsiloxane has Mn 118 kg/mol and Mw 1101 kg/mol.

Example 19

900 parts of the dimethylhydroxyl-terminated polydimethylsiloxane of Example 1 was mixed with 100 parts decamethylcyclopentasiloxane and 0.72 parts methyltrimethoxysilane (MTM). 4 parts per million (ppm) [Cl(PCl$_2$=N)$_x$PCl$_3$]$^+$ [PCl$_6$]$^-$ diluted in dichloromethane was added as catalyst. The polymerisation was carried out in a 1 l glass reactor (IKA) at 80° C. under vacuum. The polymerisation was stopped after 36 minute by the addition of 0.009 parts trihexylamine. A branched polydimethylsiloxane dissolved in decamethylcyclopentasiloxane was produced. The branched polydimethylsiloxane has Mn 47 kg/mol and Mw 78 kg/mol.

Examples 20-23

Example 19 was repeated using different conditions.
Example 20—5 parts catalyst, 0.72parts methyltrimethoxysilane, 13 minutes polymerisation time, 0.0228 parts of trihexylamine Example 21—5 parts catalyst, 1.44 parts methyltrimethoxysilane, 13 minutes polymerisation time, 0.0228 parts of trihexylamine Example 22—5 parts catalyst, 3.61 parts methyltrimethoxysilane, 14 minutes polymerisation time, 0.0228 parts of trihexylamine Example 23—5 parts catalyst, 7.21 parts methyltrimethoxysilane, 15 minutes polymerisation time, 0.0228 parts of trihexylamine The number average molecular weight Mn and the weight average molecular weight Mw of each branched polydimethylsiloxane were measured by GPC. The results, and the polydispersity index PI (ratio Mw/Mn) are shown in Table 4 below. The viscosity of the reaction product was measured by a Brookfield viscometer at 25° C. as in example 1.

TABLE 4

| Example | 20 | 21 | 22 | 23 |
|---|---|---|---|---|
| Mn (kg/mol) | 81 | 73 | 73 | 68 |
| Mw (kg/mol) | 127 | 123 | 131 | 197 |
| PI | 1.57 | 1.63 | 1.79 | 2.91 |
| Viscosity | 57840 | 47940 | 45360 | 69100 |

The invention claimed is:

1. A process for the preparation of a branched organopolysiloxane comprising reacting an alkoxysilane with a substantially linear organopolysiloxane containing at least one hydroxyl or hydrolysable group bonded to silicon, wherein the reaction is carried out in the presence of a phosphazene catalyst and a diluent selected from a hydrocarbon oil comprising from 5 to 25 carbon atoms per molecule, where the amount of diluent used in the process is 5 to 70% of the combined weight of alkoxysilane, substantially linear organopolysiloxane and diluent.

2. The process according to claim 1 wherein the substantially linear organopolysiloxane has terminal hydroxyl groups bonded to silicon.

3. The process according to claim 1 wherein the alkoxysilane comprises a trialkoxysilane of the formula R'Si(OR)$_3$, where R represents an alkyl group having 1 to 4 carbon atoms and R' represents a monovalent hydrocarbon or substituted hydrocarbon group having 1 to 18 carbon atoms.

4. The process according to claim 1 wherein the alkoxysilane comprises a tetraalkoxysilane.

5. The process according to claim 1 wherein the alkoxysilane comprises a partially condensed alkoxysilane containing on average more than two alkoxy groups per molecule bonded to silicon.

6. The process according to claim 1 wherein the phosphazene catalyst is a perchlorooligophosphazenium salt of the formula

[Cl$_3$P—(N=PCl$_2$)$_n$Cl]$^+$Z$^-$ where n has an average value in the range 1 to 10 and Z represents an anion of the formula MX$_{v+1}$ in which M is an element having an electronegativity on Pauling's scale of from 1.0 to 2.0 and valency v and X is a halogen atom.

7. The process according to claim 1 wherein the phosphazene catalyst is an oxygen-containing chlorophosphazene of the formula Cl(PCl$_2$=N)$_n$—P(O)Cl or HO(PCl$_2$=N)$_n$—P(O)Cl$_2$ where n has an average value in the range 1 to 10.

8. The process according to claim 1 wherein the phosphazene catalyst is an oxygen-containing chlorophosphazene containing organosilicon radicals and has the formula R"$_3$SiO (PCl$_2$=N)$_n$—P(O)Cl$_2$ where each R" represents a monovalent hydrocarbon or substituted hydrocarbon group having 1 to 18 carbon atoms and n has an average value in the range 1 to 10.

9. The process according to claim 1 wherein the diluent is a natural oil.

* * * * *